(12) United States Patent
Byrum et al.

(10) Patent No.: US 6,219,964 B1
(45) Date of Patent: *Apr. 24, 2001

(54) METHOD FOR IDENTIFYING GENETIC MARKER LOCI ASSOCIATED WITH TRAIT LOCI

(75) Inventors: Joseph Richard Byrum, West Des Moines; Robert Stefan Reiter, Urbandale, both of IA (US)

(73) Assignees: E. I. du Pont de Nemours and Company, Wilmington, DE (US); Asgrow Seed Co., Kalamazoo, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/826,409

(22) Filed: Mar. 27, 1997

Related U.S. Application Data (60) Provisional application No. 60/039,844, filed on Mar. 20, 1997.

(51) Int. Cl.[7] ............... A01H 1/00; A01H 1/04; C12N 15/00; C12N 5/04
(52) U.S. Cl. ............ 47/58; 47/58.03; 47/58.05; 800/278; 435/410; 435/412; 435/415
(58) Field of Search .................. 435/410, 412, 435/415; 536/23.1, 23.6; 47/58, 58.03, 58.05

(56) References Cited

U.S. PATENT DOCUMENTS

| | | | |
|---|---|---|---|
| 5,332,408 | 7/1994 | Mets et al. | 47/58 |
| 5,437,697 | * 8/1995 | Sebastian et al. | |
| 5,492,547 | 2/1996 | Johnson | 47/58 |
| 5,723,596 | 3/1998 | Cramer et al. | 536/243 |

FOREIGN PATENT DOCUMENTS

| | | |
|---|---|---|
| 0 242 062 | 10/1987 | (EP) . |
| 0 306 139 | 3/1989 | (EP) . |
| WO 97 12059 | 4/1997 | (EP) . |
| WO 89 07647 | 8/1989 | (WO) . |
| WO 95 19697 | 7/1995 | (WO) . |
| WO 95 20669 | 8/1995 | (WO) . |

OTHER PUBLICATIONS

Nucleic Acids Research, vol. 17, 1989, Tautz, pp. 6483–6471.
Crop Sci., vol. 34, Stromberg et al., 1994, pp. 1221–1225.
Plant Breed Rev., vol. 9, Stuber, 1992, pp. 37–61.
Crop Sci., vol. 34, Bernardo, 1994, pp. 20–25.
Crop Sci., vol. 27, Nienhuis et al., 1987, pp. 797–803.
Nucleic Acids Research, vol. 18, Williams et al., 1990, pp. 6531–6535.
Genetics, vol. 95, Stuber, 1980, pp. 225–236.
Genetics, vol. 116, Edwards et al., 1987, pp. 113–125.
Genetics, vol. 121, Lander and Botstein, 1989, pp. 185–199.
Genetics, vol. 132, Stuber et al., 1992, pp. 832–839.
Nature, vol. 335, Paterson et al., 1988, pp. 721–726.
Nucleic Acids Research, vol. 23, Vos et al., 1995, pp. 4407–4414.
L. M. Mansur et al., Crop Science, 36:1327–1336 (1996).
N. Hnetkovsky et al., Crop Science, Genetic mapping of loci underlying field resistance to soybean sudden death syndrome, 36:393–400 (1996).
P.J. Maughan et al., Theor Appl. Genetics, Amplified fragment length polymorphism (AFLP) in soybean: species deiversity, inheritance, and near–isogenic line analysis, 93: 392–401, (1996).
J. Rongwen et al., Theor. Appl. Genetics, The use of microsatellite DNA markers for soybean genotype identification, 90: 43–48 (1995).
E. S. Lander et al., Genetics, Mapping Mendelian Factors Underlying Quantitative Traits Using RFLP Linkage Maps, 121: 185–199 (1989).
S. D. Tanksley et al., Biotechnology, RFLP Mapping in Plant Breeding New Tools for an Old Science, 7:257–264, (1989).
K. P. Pauls, Biotechnology Advances, Plant Biotechnology for Crop Improvement, 13:673–693, (1995).
S. D. Tanksley et al., Plant Molecular Biology Reporter, Molecular Markers in Plant Breeding, 1:1 (1983).
P. Keim et al., Genetics, RFLP Mapping in Soybean: Association Between Marker Loci and Variation in Quantitative Traits, 126: 735–742, (1990).

\* cited by examiner

*Primary Examiner*—Phuong T. Bui (57) ABSTRACT

A method for identification of trait loci using genetic marker loci and the use of genetic marker loci as a selection method in a plant breeding program is disclosed. The method comprises comparing genotypic survey data to phenotypic data collected from the same entries used to create the genotypic survey and identifying genetic marker loci that are associated with traits. The method allows new and superior plants to be identified and selected for in a plant breeding program by genotyping with identified genetic marker loci.

8 Claims, 2 Drawing Sheets

METHOD FOR IDENTIFYING GENETIC MARKER LOCI ASSOCIATED WITH TRAIT LOCI

CROSS REFERENCE TO RELATED APPLICATION

This application claims the benefit of U.S. Provisional Application No. 60/039,844, filed Mar. 20, 1997.

FIELD OF INVENTION

This invention is in the field of plant breeding and molecular biology. More specifically, the invention relates to the identification of trait loci using genetic marker loci and the use of genetic markers as a selection method in a plant breeding program.

BACKGROUND OF INVENTION

Plant breeding is the art and science of increasing a plant's value through genetic manipulation. The plant breeder intermates plants with different genetic backgrounds an, attempts to identify and select progeny with superior genetic composition and hence superior phenotypic performance. A difficulty for the plant breeder is accurately determining what the best genotype is. He or she must rely on phenotypic measurements to understand the genotype.

Many traits of importance, like grain yield, are measured quantitatively. These quantitatve traits typically display non-discrete phenotypic distributions which are the result of many genetic and environmental factors. A direct consequence is that the phenotype is frequently a weak predictor of the genotype. Thus, the selection of superior genotypes can be a challenging endeavor.

Trait selection based upon genetic markers has been suggested as a more direct method of selecting superior genotypes. In order for genetic marker-based selection to be successful however, an association between marker loci and trait loci must first be established. The resolution of quantitative traits into discrete genetic factors is the first step in this process.

Numerous examples exist of the genetic dissection of quantitative traits with genetic markers (Stuber, C. W. 1992. Plant Breed. Rev 9:37–61). These and other studies attempt to identify the location of quantitative trait loci (QTLs) in relation to linked marker loci. The discovery of these genetic linkage relationships is key if markers are to be successfully used to select for linked QTLs. Once this association is established, selection based upon marker genotypes is facilitated.

There have been four general methods used to identify marker loci in linkage with and predictive of a quantitative trait. Two of these methods measure changes in marker allele frequency in response to selection. Stuber et al. (Stuber, C. W. et al., 1980. Genetics 95:225–236) is exemplary of one of these methods of analysis. Within a given population, marker allele frequencies are measured before and after selection. Significant changes in allele frequency at a marker locus is presumed to be due to linkage between marker locus and selected trait locus.

U.S. Pat. No. 5,437,697 also describes allele frequency changes as a means for identification of predictive marker loci. The marker allele frequency of elite lines is compared with the allele frequency of their progenitors. Marker loci in linkage with QTLs are identified by non-random changes in marker allele frequency among the elite lines examined. These non-random marker allele frequency changes are presumed to be due to phenotypic selection of trait loci linked to marker loci.

A third method for identifying marker-QTL relationships analyzes segregating populations derived from the intermating of two parent lines (Edwards, M. D. et al., 1987. Genetics 116:113–125; Nienhuis, J. et al., 1987. Crop Sci. 27:797–803). The parent lines are typically selected for their phenotypic and genotypic incongruence. These studies attempt to take advantage of the high degree of genetic disequilibrium present in F2, backcross and to a lesser degree recombinant inbred populations. By minimizing opportunities for recombination, marker loci need not be tightly linked to QTLs in order to establish a significant association. Marker loci linked to QTLs are identified by making locus-by-locus comparisons of the mean phenotypic performance of marker allele classes. It is assumed that marker loci with unequal phenotypic means are in linkage with one or more QTLs.

An alternative to single marker analysis was proposed by Lander and Botstein (E. S. Lander and D. Botstein, 1989. Genetics 121:185–199) and later used to map QTLs in a plant species (Paterson, A. H. et al., 1988. Nature 335:721–726.). The method, known as interval mapping, estimates the statistical likelihood of a QTL being located at pre-defined intervals between marker loci. Both single marker analysis and interval mapping use the same types of experimental populations described earlier.

All marker-based mapping methods rely on accurate determination of the phenotype. For traits with high heritability this is not a problem, but for most traits of agronomic interest, especially yield, the ability to measure the trait accurately is difficult because these traits exhibit low heritability. The heritability of a trait is defined in the broad sense as the ratio of the genetic variance to the total phenotypic variance. Many agronomic traits display low heritability; i.e., the performance of parent plants is a poor predictor of offspring performance. Thus, traits with low heritability have small genetic variance components in comparison with observed phenotypic variation. The impact on the plant breeder is that in breeding populations, the value of a plant's genetic composition is difficult to determine from agronomic trait measurements. In an attempt to maximize their discriminative abilities, breeders collect multiple measurements both from individuals related by descent and from many environments. This strategy is resource intensive because it involves the use of extensive trialing to make even small gains in plant improvement.

To improve measurements of yield and other traits with low heritability, replicated progeny and multiple environments have been evaluated (Stuber, C. W. et al., 1992. Genetics 132:823–839). Unfortunately, a truly accurate assessment of phenotype requires far greater replication across many spatial and temporal environments.

A more serious drawback exists with studies using experimental populations. These studies are limited in context in that a maximum of only two alleles are segregating. Accordingly, analyses can only compare the effect of one allele against the second. If these alleles do not exhibit sufficient phenotypic incongruence, then the QTL is not identified. In reality there are likely many other alleles, some with positive phenotypic effects, within the species which, if identified, could be exploited by the plant breeder.

Pedigree-based analysis as disclosed in U.S. Pat. No. 5,437,697 attempts to overcome the shortcomings of earlier methods. A difficulty with this and other allele frequency based approaches is the dependence upon phenotypic selection as the driving force for allele frequency changes. Alleles with strong phenotypic effects will consistently be selected in segregating breeding populations. These QTLs will readily be identified using allele frequency-based approaches. However, loci with alleles with only subtle phenotypic effects will likely only be selected occasionally. Many QTLs containing these potentially desirable alleles will therefore not be detected.

A further handicap when using the method disclosed in U.S. Pat. No. 5,437,697 is the ability to only detect associations with trait loci for overall agronomic fitness. Plant breeders select for a plurality of traits simultaneously, and chosen individuals are represented by their composite performance. Depending upon the emphasis, new varieties could embody the improvement of a specific phenotypic weakness (e.g., disease resistance or a general improvement in yield). The method is thus fully dependent upon the whims of plant breeding to alter allele frequencies. The ability to detect loci associated with specific phenotypic traits is impaired.

A result of the various drawbacks to previous methods of identifying significant marker-QTL associations is that relatively few QTLs are identified for complex quantitative traits like yield, and inconsistencies in marker-QTL associations are found. The experiments of Stromberg et al., (Stromberg, L. D. et al., 1994. Crop Sci. 34:1221–1225) are particularly illustrative of these difficulties. In their study, first eight and later ten QTLs were identified for yield, in all likelihood a fraction of the true number of QTLs affecting yield. Despite re-mapping in lines derived directly from the original mapping population, only one marker-QTL association was in common between the early and later generation test.

Once marker-QTL relationships are established, marker loci are used as predictors of the trait(s) of interest. This predictive information is used in two ways. First, using genotypic germplasm survey data, parental lines may be chosen for their favorable genotypic composition. Second, segregating progeny in breeding populations may be selected based upon their similarity to the genotype predicted to have the best phenotypic performance (Stomberg, L. D. et al., 1994. Crop Sci. 34:1221–1225).

An alternative use for marker information as a yield predictor is as an estimator of genetic incongruence. Using a germplasm survey of parental lines, Bernardo (Bernardo, R. 1994. Crop Sci. 34:20–25) used restriction fragment length polymorphisms to estimate co-ancestry. This information, along with yield information, was used to predict test cross yields in maize. A similar analysis using marker incongruence and yield data is also described by Johnson (U.S. Pat. No. 5,492,547). These studies do not use markers as a selection tool, but instead attempt to use marker data to reduce the amount of costly yield trialing.

SUMMARY OF INVENTION

A method for identifying a genetic marker locus associated with a trait locus from a crop species has been discovered. The method comprises: a) creating a genotypic survey for a crop species using germplasm of multiple ancestry, the survey created using genetic markers, wherein individual entries of the germplasm survey are not members of a segregating population created for the purposes of the analysis; b) comparing the genotypic survey to phenotypic data collected on the same entries used to create the genotypic survey or their progeny; c) estimating the association between genetic marker loci and trait loci; and d) identifying a genetic marker locus that is associated with the trait locus.

In another embodiment, the instant invention comprises a method for identifying a genetic marker locus associated with a trait locus from a crop species grown in a specific environment, the method comprising: a) creating a genotypic survey for a crop species grown in a specific environment using germplasm of multiple ancestry, the survey created using genetic markers, wherein individual entries of the germplasm survey are not members of a segregating population created for the purposes of the analysis; b) comparing the genotypic survey to phenotypic data collected on the same entries used to create the genotypic survey or their progeny; c) estimating the association between genetic marker loci and trait loci; and d) identifying a genetic marker locus that is associated with the trait locus when the crop species is grown in the specific environment.

Preferred genetic markers that are useful for practice of the instant invention include restriction length polymorphisms (RFLPs), random amplified polymorphic DNAs (RAPDs), simple sequence repeats (SSRs), AFLPs, and allozymes.

The method allows new and superior plants to be identified and selected for in a plant breeding program by genotyping with identified genetic marker loci. The method is particularly applicable to crop species for which extensive trait data from plant breeding programs exists, such as soybean, corn, sunflower, rapeseed, wheat, barley, oat, rice and sorghum, tomato, potato, cucumber, onion, carrot, common bean, pepper, and lettuce. However the instant method is applicable to any crop species through de novo creation of both a genotypic germplasm survey and a trait data set. The instant method is particularly applicable to traits with low heritability such as yield, however the identification and use of genetic marker loci to select for any trait is possible.

For broad application to all traits and crop species, it is desirable that the number of entries in the survey is greater than forty and representative of more than twenty ancestries, especially in the analysis of low heritability traits. The use of fewer entries and/or ancestries reduces the ability to detect and estimate accurately the phenotypic effect predicted by a marker allele.

DETAILED DESCRIPTION OF THE INVENTION

For the purposes of this disclosure we define the following terms:

Breeding. The art and science of improving a species of plant or animal through controlled genetic manipulation.

Trait. An observable characteristic of an organism.

Trait Allele. A gene with a defined contribution to an observed characteristic.

Trait Locus. A genetically defined location for a collection of one or more genes (alleles) which contribute to an observed characteristic.

Agronomic Performance. The expression of those traits which have an impact on the harvestable yield of a given plant variety. Agronomic traits generally are measured in a quantitative fashion and exhibit non-discrete phenotypic distributions.

Yield. The productivity per unit area of a desired plant product.

Lodging Resistance. The ability of a plant to remain upright until the time of harvest, thus permitting complete harvesting of the grain.

Height. The length of a plant from the ground to canopy top.

Maturity. The time required for a plant to attain a state of harvestability.

Disease Resistance. The ability of a plant to tolerate attack by either a fungal, bacterial or viral pathogen.

Pest Resistance. The ability of a plant to tolerate attack by either insects or nematodes.

Nutrient Deficiency. A condition manifested by the sub-optimal growth of a plant due to inadequate supply of an essential element.

Grain Composition. Those characteristics which describe the harvested grain. These include both the quantity and the quality of specific grain characteristics such as protein, oil, carbohydrate and water.

Crop Species. A plant species which is cultivated by man in order to produce a harvestable product. As used herein, crop species include soybean, corn, sunflower, rapeseed, wheat, barley, oat, rice and sorghum, tomato, potato, cucumber, onion, carrot, common bean, pepper, and lettuce.

Phenotypic Data. A set of trait observations made from one or more individuals.

Phenotypic Value. A measure of the expected expression of an allele at a trait locus. The phenotypic value of an allele at a trait locus is dependent upon its expressive strength in comparison to alternative alleles. The phenotypic value of an individual, and hence its phenotypic potential, is based upon its total genotypic composition at all loci for a given trait.

Genetic Marker. Any morphological, biochemical, or nucleic acid-based phenotypic difference which reveals a DNA polymorphism. Examples of genetic markers includes but is not limited to RFLPs, RAPDs, AFLPs, allozymes and SSRs.

Genetic Marker Locus. A genetically defined location for a collection of one or more DNA polymorphisms revealed by a morphological, biochemical or nucleic acid-bred analysis.

Genetic Marker Allele. An observed class of DNA polymorphism at a genetic marker locus. For most types of genetic markers (RFLPS, allozymes, SSRs, AFLPs, RADs), alleles are classified based upon DNA fragment size. Individuals with the same observed fragment size at a marker locus have the same genetic marker allele and thus are of the same allelic class.

Genotyping. The process of determining the genetic composition of individuals using genetic markers.

Genotype. The allelic composition of an individual at genetic marker loci under study.

Genotypic Survey. A database of genetic information based upon genetic marker analysis.

Germplasm of Multiple Ancestry. A collection of entries composed of strains, lines, cultivars, varieties, synthetics, hybrids, plant introductions or their derivatives, wherein entries are derived from more than one shared genetic derivation.

Segregating Population. A genetically heterogeneous collection of plants of the same genetic derivation and with consequent inter-relatedness. Examples of segregating populations include but is not limited to backcross, recombinant inbred or filial generation populations.

Breeding Population. A genetically heterogeneous collection of plants created for the purpose of identifying one or more individuals with desired phenotypic characteristics.

Transgressive Segregants. Individuals whose phenotype exceeds the phenotypic variation predicted by the parents.

Ideal Genotype. A theoretical genotype, based upon available genetic marker information, predicted to express the most favorable phenotypic response.

Quantitative Trait Loci (QTLs). The locations of genes whose biochemical and/or regulatory functions affect the phenotype of a numerically measured trait.

Restriction Fragment Length Polymorphism (RFLP). A DNA-based genetic marker in which size differences in restriction endonuclease generated DNA fragments are observed via hybridization (Botstein, D. et al., 1980. Am. J. Hum. Genet. 32: 314–331.

Random Amplified Polymorphic DNA (RAPD). A DNA amplification-based genetic marker in which short, sequence-arbitrary primers mediate amplification. The resulting amplification products are size-separated and differences in amplification patterns observed (Williams, J. G. K. et al., 1990. Nucleic Acids Res. 18:6531–6535).

Simple Sequence Repeat (SSR). A DNA amplification-based genetic marker in which short stretches of tandemly repeated sequence motifs are amplified. The resulting amplification products are size separated and differences in length of the nucleotide repeat are observed (Tautz, D. 1989. Nucleic Acids Res. 112:4127–4138).

AFLP. A DNA amplification-based genetic marker in which restriction endonuclease-generated DNA fragments are ligated to short DNA fragments which facilitate the amplification of the restricted DNA fragments (Vos, P. et al., 1995. Nucleic Acids Res. 23:4407–4414.). The amplified fragments are size separated and differences in amplification patterns observed.

Allozymes. Enzyme variants which are electrophoretically separated and detected via staining for enzymatic activity (Stuber, C. W. and M. M. Goodman. 1983. USDA Agric. Res. Results, Southern Ser., No. 16).

Marker-Assisted Selection. The use of genetic marker alleles to identify and select plants with superior phenotypic potential. Genetic marker loci determined previously to be associated with a trait locus or trait loci are used to uncover the genotype at trait loci by virtue of linkage between the genetic marker locus and the trait locus. Plants containing desired trait alleles are chosen based upon their genotypes at linked genetic marker loci.

The present invention provides a method for identifying genetic marker loci that are associated with DNA segments containing trait loci. The discovery of these linkage Associations facilitates the use of these genetic marker loci as predictors of both the genotypic composition of plants in breeding populations as well as their phenotypic potential.

Specifically, the method uses genotypic information derived from the genetic marker analysis of several breeding lines and varieties with diverse ancestry. This genotypic germplasm survey is used in an analysis with phenotypic trait data collected on either the same lines in the genotypic survey or trait data from their offspring. The phenotypic trait data is represented by measurements collected during the breeding history of each entry in the survey. The mean phenotypes of each allelic class at a marker locus are compared. Marker loci with allelic classes having dissimilar phenotypic performance are identified as being in linkage with trait loci affecting performance. Those genetic marker alleles, in cis linkage with trait alleles conferring a desired phenotypic response, may be selected for in breeding programs.

The invention takes advantage of the extensive phenotypic data collected and used in conventional plant breeding programs. By way of example, yield for a successful soybean line typically is measured several hundred times during the development of the line. If one examines 300 lines each with 300 yield measurements, there would be 90,000 yield data points available for analysis. The estimated yield, effect for each marker allele is thus based upon several hundred (for low frequency alleles) to tens of thousands (for high frequency alleles) yield measurements.. Because the yield data is collected from many lines developed over several years, the phenotypic effect of an allele is based upon extensive temporal and spatial replication. By insuring adequate representation of known alleles, the phenotypic effects of all alleles may be tested.

According to the method of the invention any genetic marker type may be used. Those skilled in the art will recognize that the various genetic markers which may be used includes but is not limited to, restriction fragment length polymorphisms (RFLPs), random amplified polymorphic DNAs (RAPDs), simple sequence repeats (SSRs), AFLPs, various single base pair detection methods, allozymes, and phenotypic markers.

The method may be applied to any trait of interest to the plant breeder and is particularly well suited for the analysis of traits exhibiting low heritability. Large trait data sets are used to offset the poor precision of individual trait measurements. Traits which exhibit high heritability may also be exploited using the instant method. Since these traits can be measured with greater precision, a smaller trait data set is required to successfully use the instant method.

The genetic marker loci that are identified using the instant method can be used in the marker-assisted selection of plants in a breeding program. Selection could be based upon the genotype of one or more marker loci. It is obvious to those skilled in the art that various predictive models, using marker data alone or in conjunction with phenotypic data, may be developed to determine the breeding value of individual genotypes. Individual marker alleles may also be weighted based upon their predictive value for the phenotype of interest. These models may be used to predict and select for the most desirable genotypes present in a current breeding population, to identify parent lines with a probability of producing desirable progeny, and to predict ideal genotypes. Moreover, the instant invention affords the ability to select for plants comprising several desirable traits concurrently.

Another embodiment of the present invention is the ability to predict and select for genotypes adapted to particular locations and environments. By analyzing the phenotypic data collected from entries grown in specific locations or in specific environments, genetic marker loci and their associated trait loci affecting performance in a specific environment can be identified. In this way the performance of a trait allele in a specific environment can be predicted and the most desired trait alleles identified. By selecting the associated genetic marker allele, new varieties with superior performance in specific environments or locations can be developed.

The present invention relates to the identification of genetic marker loci linked to trait loci and the subsequent use of these marker loci in the development of superior lines in a breeding program. First, a genotypic germplasm survey is conducted on a collection of entries from the same species. Entries in the survey are represented by parental materials and breeding lines of diverse ancestry. Any genetic marker type could be used to practice the invention; however it is desirable that many marker loci are used and that the marker type reveals a sufficient level of polymorphism.

For example, if RFLP analysis is used to conduct the genotypic germplasm survey, DNA is isolated from plant tissue of each of the entries and digested with a restriction endonuclease. The DNA is next size separated using agarose gel electrophoresis, then transferred and immobilized on either nylon membrane or nitrocellulose. Using a cloned DNA fragment (DNA marker) as a hybridization probe, complementary DNA fragments immobilized on the membrane are observed.

For each of the methods employing nucleic acid-based genetic markers, the relative sizes of the observed DNA fragments (marker alleles) are compared between entries. For each DNA marker, entries having the same observed DNA fragment size are recorded as having the same genetic marker allele. Thus, for each marker, entries are classified into one of the observed genetic marker allele size classes.

The second step of the method is the comparison of the genetic survey data with a trait data set collected on either the same entries or their progeny. Typical trait data sets can be generated de novo, or may be available as a result of the routine data collection which occurs in plant breeding programs. For traits with low heritability, it is desirable that the trait data set be large and be replicated both temporally and spatially.

Using least squares statistical methods, genetic marker loci are examined individually in order to estimate the association between individual genetic marker loci and trait loci, thus leading to the discovery of genetic marker loci that are associated with trait loci. These associations are the result of genetic linkage between genetic marker loci and trait loci and are identified by calculating and comparing the, mean trait performance for each allelic class at a genetic marker locus. Preferred marker locus/trait locus associations are identified at a significance level of $p<0.05$, but could be identified using higher probability thresholds.

Because the trait data is typically collected over several years and many locations, it is desirable to reduce the non-genetic variation in order to maximize the ability to detect significant differences between marker allele classes. This can be accomplished by inclusion of non-genetic variance partitioning and covariate normalization of the data set. It is obvious to those skilled in the art that either alternative statistical or simulation procedures could be employed to detect marker locus/trait locus associations using the instant method. These procedures include but are not limited to alternative least squares models and methods, multivariate models and methods, simulation procedures, and maximum likelihood procedures.

The mean phenotypic values calculated for each allele class at a genetic marker locus re estimators of the phenotypic value or breeding value of cis-linked alleles tat a trait locus. Therefore the superior allele or alleles at trait loci are identified and may be selected for using genetic marker locus data. By genotyping, parental lines with a high frequency of desired and complementary alleles at marker loci could be identified and chosen for crossing. Breeding populations lay also be genotyped and individuals identified with expected superior phenotypic performance based upon their genotypic composition.

Certain genetic marker systems such as AFLPs and RAPDs are primarily dominant genetic marker systems. With dominant genetic markers, only one allelic class is observable in an individual even if the individual is genetically heterozygous at the marker locus examined. Heterozygotes and homozygotes are therefore not distinguishable. In addition, with AFLPs and RAPDs the number of possible allele classes is usually limited to two per locus; the observable allele is one allele class and all other alleles which are not observable are the second allele class. In contrast, RFLPs and SSRs are generally co-dominant marker systems. If an individual is heterozygous at a marker locus, both allelic classes can be observed and complete genetic characterization of individuals is possible. With RFLPs or SSRs many allele classes are typically observed. Accordingly, when a collection of lines of diverse ancestry are analyzed using AFLPs or RAPDs, the lines are categorized by either having a band (observed allele) or lacking that band (all other alleles) following electrophoretic separation and analysis of amplified DNA fragments. In the practice of the instant method, the phenotypic value of the observed allele is determinable, along with a composite phenotypic value for the collection of unobserved alleles. The value of a linked trait allele is thus measured against the average value of all other alleles present at a trait locus.

This contrasts analyses that employ co-dominant marker systems (e.g., RFLPs and SSRs) wherein alternative alleles are observed. Here, the number of alleles which can be distinguished from each other is dependent upon the degree of polymorphism at the marker locus and the level of allele resolution afforded by the technical steps employed. The phenotypic value of each observed allele can be determined using the instant method and thus the phenotypic value of individual trait alleles can be compared.

The instant method possesses three key advantages over the art in identifying and using genetic marker alleles for the selection of trait alleles. First, by taking advantage of the large amount of trait data collected for each entry in plant breeding programs, the ability to identify and accurately estimate a marker allele/trait allele association is dramatically improved because of the larger size of the trait data set. This is in contrast with conventional segregating population analyses which used only limited replication and testing locations.

Second, by testing entries of multiple ancestry, the genetic context in which marker/trait associations are made is superior. By testing the value of an allele in multiple genetic backgrounds, a more accurate and more valuable phenotypic value is estimated. Many if not all possible alleles at each locus are analyzed. This is in contrast with conventional segregating population analyses where typically only two alleles are tested. An additional advantage is the genetic context under which the phenotypic contribution of trait alleles is estimated. When a superior allele is identified by virtue of a significant marker locus/trait locus association, the estimated effect of substituting that allele for another allele at the trait locus is not overestimated. This is because the effect is estimated using a large diverse collection of entries as the population of reference. Selection for that allele should result in phenotypic improvement near to that predicted from the analysis. In previous methods, using segregating populations of limited ancestry, the phenotypic value of an allele is estimated within the context of a limited genetic background (i.e., only a limited set of trait loci which have contrasting alleles). Over-estimation of the effect of a trait allele is often the result and selection for the same allele in other populations is not likely to result in the same phenotypic improvement. This overestimation is especially problematic because one of the parent lines selected is often agronomically inferior, but is chosen because of its phenotypic and genotypic incongruence.

Finally, by using the instant method to detect marker locus/trait locus associations, only genetic marker loci in close linkage to trait loci are identified. This is because entries tested in the method are typically the product of several breeding cycles and several opportunities for recombination between loci have occurred. Although this makes the discovery of marker locus/trait locus linkage associations prohibitive if marker loci are loosely linked, it is advantageous when using identified markers for marker-assisted selection in new breeding populations; this is a primary purpose for the instant method. In contrast, prior art methods use segregating populations wherein linkage disequilibrium is maximized; i.e., the ability of detecting loose marker locus/trait locus linkage associations is maximized. Using the identified markers as a selection tool in other populations is thus problematic because the cis linkage between genetic marker allele and desired trait allele is less likely to exist.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLE I

Identification of Trait Loci with Alleles Conferring Superior Yield Performance in Soybean Genotypic germplasm survey development A total of 314 soybean (*Glycine max*) varieties, plant introductions (PIs), and breeding lines were surveyed using 16 RFLP probes. These probes, found in Table I, were previously deposited at the American Type Culture Collection (ATCC), Manassas, Va.

TABLE 1

RFLP PROBES USED TO CONDUCT GENETIC SURVEYS OF SOYBEAN LINES

| Probe | Accession No. |
|---|---|
| 1202 | ATCC 97082 |
| 1203 | ATCC 97083 |
| 1318 | ATCC 97084 |
| 1329 | ATCC 97085 |
| 1342 | ATCC 97086 |
| 1443 | ATCC 97088 |
| 1450 | ATCC 97089 |
| 1487 | ATCC 97090 |
| 1492 | ATCC 97091 |
| 1503 | ATCC 97092 |
| 1522 | ATCC 97093 |
| 1525 | ATCC 97094 |
| 1529 | ATCC 97095 |

TABLE 1-continued

RFLP PROBES USED TO CONDUCT GENETIC
SURVEYS OF SOYBEAN LINES

| Probe | Accession No. |
|---|---|
| 1587 | ATCC 97096 |
| 1593 | ATCC 97097 |
| 1596 | ATCC 97098 |

Soybean leaf tissue was collected from greenhouse-grown plants and used as a DNA source. RFLP analysis was carried out as described in U.S. Pat. No. 5,437,697.

Each marker locus was scored independently and a genotypic code was assigned to each genetic marker allele class (Table II; separate marker allele classes are comprised of restriction fragments of equivalent length). Heterozygous classes were assigned using additional codes. Therefore entries with the same genotypic code at a locus shared the same RFLP pattern and were considered to be genetically identical at that locus (Table II).

Yield data collection

The yield data set spans ten years of yield testing in Asgrow Seed Co.'s breeding trials. Individual entries were not tested in each of the ten years represented; rather, data exists for entries in those years during which entries were being actively evaluated in the breeding program. Each year, entries were grown in tests with one to three test sets per location. Entries were replicated two to three times within a test set. Locations were chosen to be both representative of a diverse set of growing environments as well as reflective of the various soybean maturity groups. An entry would have been grown at a minimum of six and a maximum of sixty locations in any given year with a median of ten locations per year.

Determination of genetic marker loci linked to loci controlling yield

Using all of the replicated yield data for each entry, the mean yield was calculated for each entry by test by year combination. These mean values were used in the actual analysis. Marker loci were tested independently using separate analyses in which the number of allelic classes examined at a locus was dependent upon the number of RFLP alleles observed at that locus. Each marker was thus tested in an analysis of variance using the following model:

$$Y_{ijkl}=\mu+\alpha_i+\tau_j+\rho_k+\beta(X_{ij}-X\ldots)+(\alpha\tau)_{ij}+(\alpha\rho)_{ik}+(\alpha\tau\rho)_{ijk}+\epsilon_{ijkl}$$

where:

$Y_{ijkl}$=yield of the $ijkl^{th}$ entry;

$\mu$=overall mean;

TABLE II

CODED RFLP MARKER GENOTYPES OF SOYBEAN LINES
(Genotypes coded with either a 1, 2, or 3 represent three different homozygous RFLP allele classes. Genotypes coded with a ½ represent an allele 1/allele 2 heterozygote. Missing genotypes are coded with a 0 and for the ideal line non-significant loci are coded as ns.)

| LOCUS | IDEAL LINE | A4997 | A4906 | A3205 | A3127 | A4271 | A3966 | A5474 | A1937 | PI54610 | ROANOKE | A3307 |
|---|---|---|---|---|---|---|---|---|---|---|---|---|
| 1203 | 2 | 2 | 2 | 2 | 2 | ½ | ½ | 2 | 1 | 1 | 2 | ½ |
| 1529 | 1 | 1 | 1 | 1 | 1 | 1 | 1 | 1 | 1 | 1 | 1 | 1 |
| 1443 | 1 | 2 | 2 | 1 | 1 | 1 | 1 | 2 | 1 | 1 | 2 | 1 |
| 1329 | ns | 1 | 1 | 2 | 2 | 2 | 2 | 1 | 3 | 2 | 2 | 2 |
| 1522 | 2 | 2 | 2 | 2 | 2 | 2 | 1 | 1 | 2 | 1 | 1 | 2 |
| 1596 | 2 | 2 | 2 | 2 | 2 | 2 | 2 | 2 | 2 | 2 | 1 | 3 |
| 1525 | 1 | 1 | 1 | 1 | 1 | 1 | 1 | 1 | 1 | 1 | 1 | 1 |
| 1487 | ns | 1 | 1 | 1 | 1 | 1 | 1 | 2 | 1 | 1 | 1 | 1 |
| 1503 | 1 | 1 | 0 | 1 | 1 | 1 | 1 | 1 | 1 | 1 | 1 | 2 |
| 1202 | 1 | 1 | 1 | 1 | 1 | 1 | 1 | 1 | 2 | 1 | 1 | ½ |
| 1450 | ns | 2 | 0 | 1 | 1 | 1 | 1 | 0 | 1 | 2 | 1 | 1 |
| 1492 | ns | 1 | 1 | 2 | 1 | 2 | ½ | 2 | 2 | 2 | 2 | 1 |
| 1587 | 1 | 2 | 0 | 1 | 1 | 1 | 1 | 1 | 1 | 1 | 1 | 1 |
| 1593 | 2 | 3 | 2 | 1 | 1 | 1 | 1 | 3 | 2 | 1 | 1 | 1 |
| 1342 | 2 | 0 | 0 | 0 | 0 | 0 | 0 | 0 | 0 | 0 | 0 | 0 |
| 1318 | ns | 1 | 1 | 1 | 1 | 1 | 1 | 1 | 1 | 1 | 1 | 1 |

| LOCUS | IDEAL LINE | CNS | MANDARIN | A4595 | MUKDEN | HARROW | MANCHU | TOKYO | RICHLAND |
|---|---|---|---|---|---|---|---|---|---|
| 1203 | 2 | 1 | 2 | 1 | 2 | 1 | 1 | 1 | 1 |
| 1529 | 1 | 1 | 1 | 1 | 1 | 1 | 1 | 1 | 1 |
| 1443 | 1 | 2 | 2 | 1 | 0 | 1 | 2 | 2 | 0 |
| 1329 | ns | 1 | 2 | 2 | 0 | 2 | 2 | 2 | 0 |
| 1522 | 2 | 1 | 1 | 1 | 1 | 1 | 2 | 1 | 1 |
| 1596 | 2 | 2 | 1 | 1 | 1 | 1 | 1 | 1 | 1 |
| 1525 | 1 | 1 | 1 | 1 | 0 | 2 | 2 | 1 | 0 |
| 1487 | ns | 1 | 1 | 1 | 1 | 2 | 1 | 1 | 1 |
| 1503 | 1 | 1 | 3 | 0 | 0 | 1 | 3 | 3 | 0 |
| 1202 | 1 | 1 | 3 | 1 | 3 | 2 | ½ | 1 | 2 |
| 1450 | ns | 1 | 1 | 1 | 0 | 2 | 2 | 1 | 0 |
| 1492 | ns | 1 | 2 | 1 | 2 | 1 | 2 | 2 | 2 |
| 1587 | 1 | 1 | 2 | 1 | 0 | 2 | 2 | 1 | 0 |
| 1593 | 2 | 1 | 3 | 1 | 2 | 1 | 1 | 1 | 1 |
| 1342 | 2 | 0 | 0 | 0 | 0 | 0 | 0 | 0 | 0 |
| 1318 | ns | 1 | 1 | 1 | 1 | 1 | 1 | 1 | 2 |

$\alpha_i$=marker allele effects;

$\tau_j$=year effects;

$\rho_k$=maturity effects;

$\beta$=regression coefficient of Y on X where $X_{ij}$=test plot yield means; and $\epsilon_{ijkl}$=error.

As shown in the model, test plot means were used as a covariate in order to reduce the amount of non-genetic variation. As a result, F tests were conducted using the adjusted mean yields for alleles at a marker locus. This data normalization was useful for two reasons: 1) to minimize the effect of varieties being yield tested in non-overlapping years and locations and 2) to remove the potentially confounding effect from selection improving the average yield of later generation entries. In addition, because of the unbalanced nature of the data sets, least square means were calculated to estimate the effects predicted by each marker allele.

Table III presents the analysis of variance results for marker 1443 which is illustrative of the instant method.

TABLE III

ANALYSIS OF VARIANCE RESULTS AND LEAST SQUARE MEANS OF SOYBEAN YIELD ACROSS ALL REPRESENTED MATURITY GROUPS WITH MARKER 1443

| Source of Variation | Degrees of Freedom | Mean Square | F value | Prob. |
|---|---|---|---|---|
| Marker 1443 | 2 | 1.714 | 10.799 | 0.000 |
| Maturity | 4 | 0.535 | 3.369 | 0.009 |
| Year | 8 | 1.116 | 7.033 | 0.000 |
| Plot Covariate | 1 | 10530.0 | 66338.7 | 0.000 |
| Maturity* 1443 | 8 | 0.960 | 6.050 | 0.000 |
| Year* 1443 | 15 | 0.863 | 5.434 | 0.000 |
| Year* Maturity | 32 | 1.531 | 9.646 | 0.000 |
| Y*M* 1443 | 33 | 1.091 | 6.867 | 0.000 |
| Error | 24522 | 0.159 | | |

A marker locus was considered to be linked to and predictive of yield if the marker locus F-test was significant at the $p<0.05$ level. As shown in Table III, marker 1443 was able to explain a significant amount of the variation observed for soybean yield ($p=0.000$); therefore one or more trait loci affecting yield are predicted to be in linkage with marker 1443.

The remaining fifteen marker loci were analyzed in a similar fashion. The model used to analyze each of the sixteen markers was the same with the exception that the numbers of entries, locations, maturity groups, and years varies depending upon the frequency of missing phenotypic and genotypic data.

Once marker locus was declared significantly associated with soybean yield, the next step is the determination of which marker alleles predict the highest yield. To compare the value of different marker alleles and their associated trait alleles, least square mean yields were calculated for each allele class at a marker locus. These mean yields are estimates of the average yield performance across all environments expected for each marker allele class. At a marker locus, the allele predicting the best soybean yield would therefore have the highest calculated mean yield. These least square mean yields (average yield) for each allele class observed at marker locus 1443 are presented in Table IV.

TABLE IV

LEAST SQUARE MEAN YIELDS FOR EACH ALLELE CLASS OBSERVED AT MARKER LOCUS 1443

| Allele | Average Yield (kg/ha +/- std err) |
|---|---|
| 1 | 4.0172 +/- 0.005 |
| 2 | 3.9627 +/- 0.012 |

As can be seen in Table IV, the best allele for soybean yield at marker 1443 is predicted to be allele 1.

The method of the instant invention therefore allows the identification of marker loci associated with soybean yield. It also identifies which genetic marker allele predicts the best yield performance at each marker locus.

EXAMPLE II

Identification of Trait Loci with Alleles Conferring Superior Soybean Yield Performance in Specific Environments The yield performance of soybean varieties is highly dependent upon the environment in which those soybean varieties are grown. Depending upon the genetic composition of the soybean plants, soybeans may respond either favorably or unfavorably to the environment in which they are grown. This interaction of genotype with environment has resulted in the breeding of soybeans specifically adapted to different environments. These environments include abiotic stresses like drought or geographic changes which affect soybean maturity requirements. Because of the importance in breeding soybeans specifically adapted to different environments, it would be of value to identify those genetic marker alleles which predict superior performance in specific environments.

Identification of genetic marker alleles which predict superior yield in specific environments examination of model interactions An examination of the marker-by-marker analyses described in Example I was performed. In many instances, (see Table III for example), significant interactions ($p<0.05$) were found between marker loci and either maturity and/or year. These interactions are a measure of the responsiveness of individual alleles to unique growing environments categorized by geographic region (maturity) and growing season (year). In Table III, these interactions (maturity*1443, year*1443) are highly significant for marker 1443. Therefore each trait allele linked to a marker 1443 allele does not have consistent yield effects in different environments.

Figure 1:
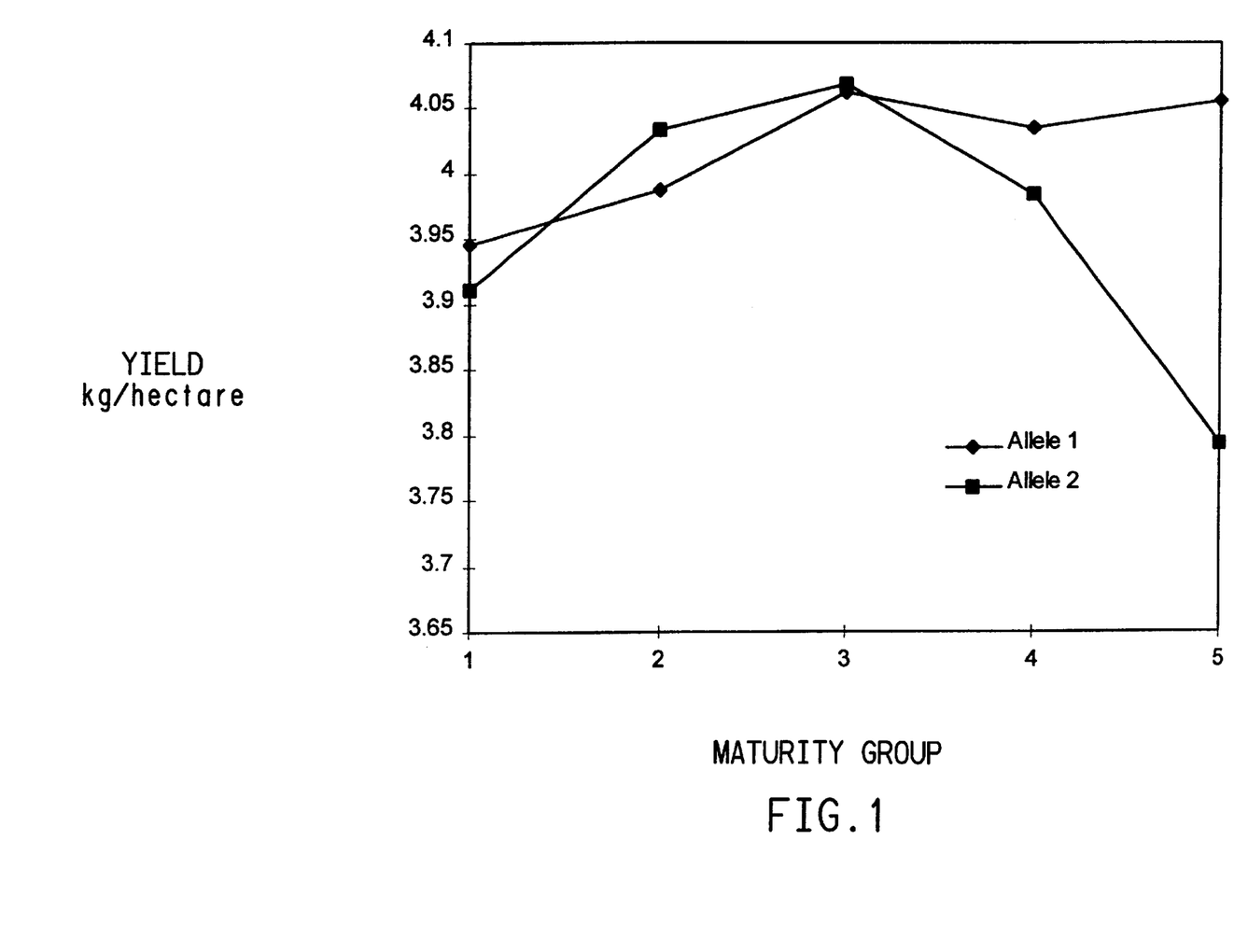
FIG. 1 is a plot of the adjusted yield calculated for each allele revealed by marker 1443 versus maturity group in soybean. This figure illustrates the phenotypic response of various trait alleles, linked to corresponding genetic marker alleles, to different geographic regions defined by soybean maturity groups.

In order to determine which allele is best suited to a specific maturity, the mean yields predicted by each genetic marker allele within each maturity group were calculated. By plotting the mean yields for each allele at marker 1443 against each maturity group from which they were calculated, one can clearly see the response of each allele as one moves from north to south across the U.S. soybean growing landscape (FIG. 1). Allele 1 exhibits consistent yield across maturity groups, whereas allele 2 appears to be best suited for maturity groups 2 and 3. In maturity group 5, the plant breeder is best served by using marker selection for allele 1 if higher yield is an objective.

By examining the mean yields estimated for each genetic marker allele within each maturity group, the best genetic marker allele and its associated trait allele can be identified for each geographic environment (as defined by maturity group). The method therefore can be used to identify and select trait alleles important for a geographic region by selecting for those alleles which exhibit high yield in a desired geographic region.

It should also be noted that geographic regions can be defined in other ways, including soil-type, average rainfall received, average heat units received, latitude or any other method of spatial classification could be used in the data analysis. These factors could be added to the general model discussed above or substituted for maturity as a factor in the model.

By way of example, as with identifying the best alleles for a maturity group, one would examine the mean yield values calculated for each allele within each soil type. The allele at each marker locus with the highest mean yield calculated for a given soil type should be selected to maximize the genotypic yield potential for that soil type.

Also of interest are the marker locus-by-year interactions. Generally soybean varieties are chosen for their ability to yield well across a range of environments within a geographic region. What is desired are varieties which show superior performance under both optimal and sub-optimal growing conditions. In a typical breeding program, where soybean lines are tested for several years, only those soybean lines which exhibit consistently superior performance are typically advanced. Therefore, despite the presence of environment-specific responsiveness by individual trait alleles, those alleles with the most consistent response across environments are generally valued. These can be identified by examining the mean performance of each marker allele by year combination and selecting for associated trait alleles with consistently superior performance from year to year.

Figure 2:
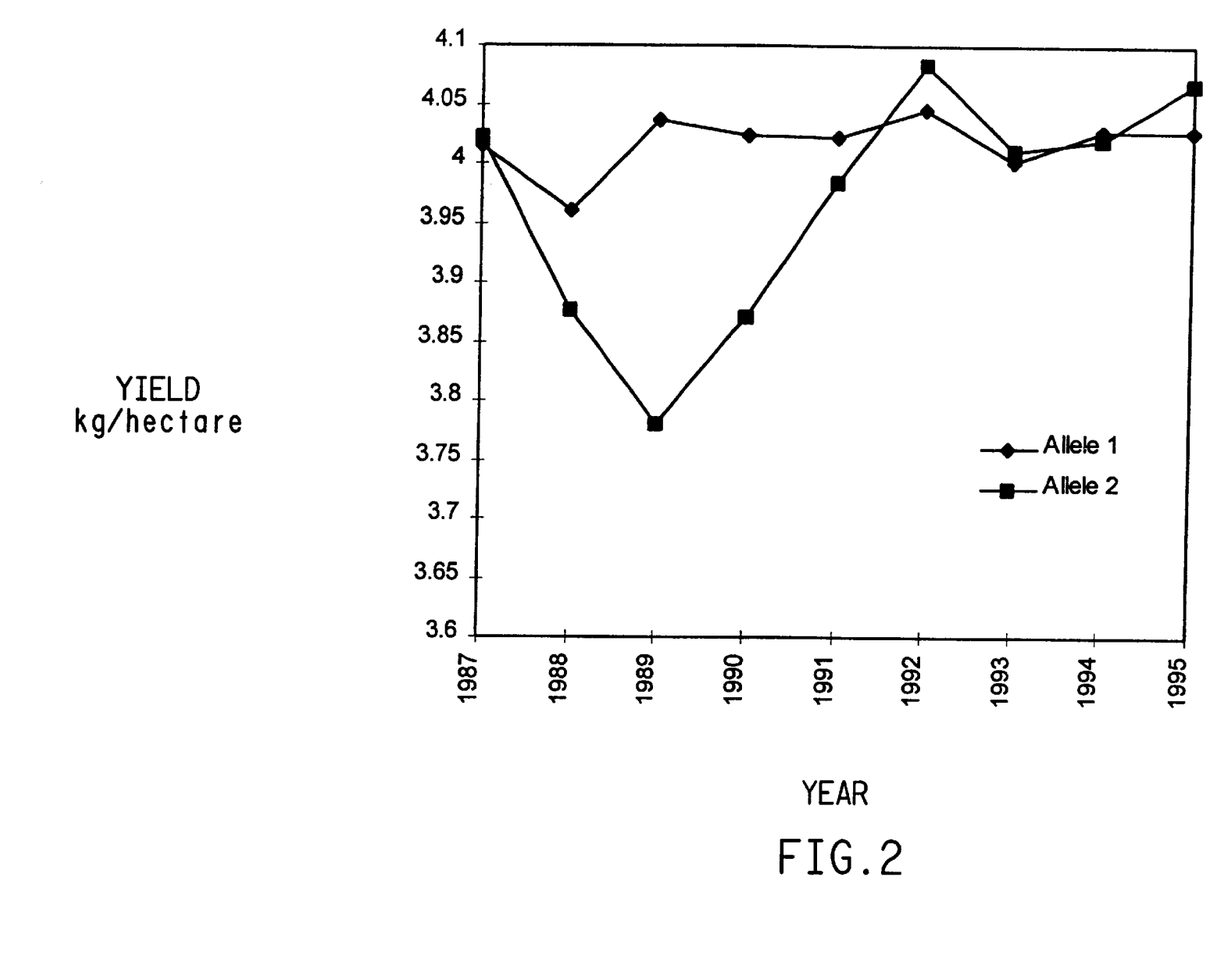
FIG. 2 is a plot of the adjusted yield calculated for each allele revealed by marker 1443 versus year in soybean. This figure illustrates the phenotypic response of various trait alleles, linked to corresponding genetic marker alleles, to different environmental conditions experienced by soybeans in each year.

The mean yields were calculated for each allele-by-year combination for marker 1443. These mean yields are plotted in FIG. 2. Examination of FIG. 2 reveals that these soybean entries with allele 1 exhibited consistent year to year yield performance in comparison to allele 2. It would therefore be advantageous to the plant breeder to select for allele 1 with marker 1443 for consistent yield performance.

The analysis could also permit the identification of trait alleles which may be uniquely important under certain environmental conditions such as drought stress. For example, by examining which genetic marker alleles predict superior yield during years with low rainfall, those alleles important for soybean drought stress could be identified.
Identification of genetic marker alleles which predict superior yield in specific environments by data set partitioning An alternative method of identifying genetic marker alleles which are predictive of superior soybean yield in certain environments is to partition the data set. By independently analyzing the data collected from a specific environment or specific region, those genetic marker alleles which are associated with favorable trait alleles for the test environment can be identified.

For example, soybean varieties are typically adapted for either the northern or southern soybean growing regions of the U.S. and are often treated as separate gene pools. It is therefore reasonable to partition the data into a northern and southern data set based upon maturity. As a result, northern or southern maturities were examined independently and used to identify and predict those alleles most valuable for soybean improvement in either the northern or southern U.S.

The model described previously in Example I was used, but only data from either entries in northern maturities or southern maturities was analyzed. Once again a marker-by-marker analysis was performed and marker loci were declared to be significantly associated with soybean yield if p<0.05. In order to determine which genetic marker allele was predictive of the highest yield, least square yield means were calculated for each genetic marker allele class. These least square means (average yield) for each allele observed at marker loci is shown in Table V for the northern maturity data set.

TABLE V

MARKER LOCI ANALYZED FOR SIGNIFICANT ASSOCIATION WITH SOYBEAN YIELD IN NORTHERN MATURITY ZONES (Marker loci which are associated with and predictive of soybean yield in northern maturity zones are indicated in bold (p < 0.05). Marker loci not indicated in bold (p > 0.05) failed to show an association with soybean yield. For each allele at marker loci, the predicted average soybean yield of entries is shown for northern maturities.)

| Locus | Allele | Average Yield (kg/ha +/- std err) |
|---|---|---|
| 1202 | 1 | 4.0678 +/- 0.006 |
| | 2 | 4.0010 +/- 0.008 |
| | 3 | 4.0654 +/- 0.062 |
| 1203 | 1 | 3.9810 +/- 0.009 |
| | 2 | 4.0185 +/- 0.005 |
| 1318 | 1 | 4.0492 +/- 0.008 |
| | 2 | 4.0311 +/- 0.014 |
| 1329 | 1 | 4.0350 +/- 0.017 |
| 1342 | 1 | 3.9964 +/- 0.006 |
| | 2 | 3.7818 +/- 0.032 |
| 1443 | 1 | 4.0335 +/- 0.005 |
| | 2 | 4.0564 +/- 0.016 |
| 1450 | 1 | 4.0655 +/- 0.006 |
| | 2 | 4.0384 +/- 0.072 |
| | 1 | 4.0357 +/- 0.004 |
| | 2 | 4.0208 +/- 0.016 |
| 1492 | 1 | 4.0408 +/- 0.005 |
| | 2 | 4.0371 +/- 0.009 |
| 1503 | 1 | 4.0696 +/- 0.007 |
| | 2 | 3.9788 +/- 0.023 |
| | 3 | 3.8866 +/- 0.036 |
| 1522 | 1 | 4.0359 +/- 0.006 |
| | 2 | 4.0352 +/- 0.005 |
| 1525 | 1 | 4.0227 +/- 0.004 |
| | 2 | 4.0388 +/- 0.012 |
| 1529 | 1 | 4.0354 +/- 0.004 |
| 1587 | 1 | 4.0679 +/- 0.007 |
| 1593 | 1 | 4.0373 +/- 0.006 |
| | 2 | 4.1176 +/- 0.056 |
| 1596 | 1 | 4.0774 +/- 0.012 |
| | 2 | 4.1179 +/- 0.012 |
| | 3 | 3.6624 +/- 0.078 |

In the north, seven marker loci (1202, 1342, 1443, 1503, 1525, 1593 and 1596) showed a significant association with soybean yield (Table V). For each significant marker locus the best allele can be identified as having the highest average yield. The highest yielding soybean variety in the north would be predicated to have a genotype composed of those marker alleles with the highest calculated average yield.

The same analysis was performed using only data from southern maturities and the least square means (average yield) for genotypes in the south are shown in Table VI.

TABLE VI

MARKER LOCI ANALYZED FOR SIGNIFICANT ASSOCIATION WITH SOYBEAN YIELD IN SOUTHERN MATURITY ZONES (Marker loci which are associated with and predictive of soybean yield in southern maturity zones are indicated in bold (p < 0.05). Marker loci not indicated in bold (p > 0.05) failed to show an association with soybean yield. For each allele at marker loci, the predicted average soybean yield of entries is shown for southern maturities.)

| Locus | Allele | Average Yield (kg/ha +/- std err) |
|---|---|---|
| 1202 | 1 | 4.0276 +/- 0.013 |
| | 2 | 3.9446 +/- 0.023 |
| 1203 | 1 | 3.9740 +/- 0.012 |
| | 2 | 3.9695 +/- 0.013 |
| 1318 | 1 | 4.0192 +/- 0.014 |
| | 2 | 3.9444 +/- 0.023 |
| 1329 | 1 | 4.0311 +/- 0.026 |

TABLE VI-continued

MARKER LOCI ANALYZED FOR SIGNIFICANT ASSOCIATION WITH SOYBEAN YIELD IN SOUTHERN MATURITY ZONES (Marker loci which are associated with and predictive of soybean yield in southern maturity zones are indicated in bold (p < 0.05). Marker loci not indicated in bold (p > 0.05) failed to show an association with soybean yield. For each allele at marker loci, the predicted average soybean yield of entries is shown for southern maturities.)

| Locus | Allele | Average Yield (kg/ha +/- std err) |
|---|---|---|
| 1342 | 1 | 3.8389 +/- 0.016 |
|  | 2 | 4.0253 +/- 0.024 |
| 1443 | 1 | 4.0431 +/- 0.017 |
|  | 2 | 3.9133 +/- 0.026 |
| 1450 | 1 | 4.1220 +/- 0.021 |
|  | 2 | 4.0469 +/- 0.065 |
| 1487 | 1 | 3.9915 +/- 0.014 |
|  | 2 | 3.9967 +/- 0.021 |
| 1492 | 1 | 3.9957 +/- 0.019 |
|  | 2 | 3.9501 +/- 0.020 |
| 1503 | 1 | 4.1258 +/- 0.018 |
|  | 2 | 4.0167 +/- 0.061 |
|  | 3 | 4.0982 +/- 0.030 |
| 1522 | 1 | 3.9660 +/- 0.014 |
|  | 2 | 3.9979 +/- 0.036 |
| 1525 | 1 | 4.0271 +/- 0.013 |
|  | 2 | 3.7564 +/- 0.058 |
| 1529 | 1 | 3.9968 +/- 0.012 |
| 1587 | 1 | 4.1194 +/- 0.022 |
| 1593 | 1 | 4.0120 +/- 0.021 |
| 1596 | 1 | 4.0686 +/- 0.019 |
|  | 2 | 4.1299 +/- 0.023 |

In the south, five marker loci (1342, 1443, 1492, 1525 and 1596) were associated with higher soybean yield (Table VI). At each significant marker locus, those marker alleles which are associated with the highest yielding trait alleles have the largest average yield. By selecting for the best allele at each significant marker locus, higher yielding southern varieties could be developed.

By partitioning the data set a unique set of marker loci can be identified for each environment. A comparison of Tables V and VI shows that a unique set of marker loci were identified in each data set. Even in instances where the same marker was identified as being significantly associated with yield, the most favorable allele was not always the same. For example, at marker locus 1342, allele 1 predicts superior yield in the north yet in the south allele 2 is preferred.

Data sets can be partitioned using other criteria. For example, the data could be partitioned according to growing-degree days, soil type, or average rainfall. For each type of environment, those marker alleles which predict superior yield performance can thus be identified.

EXAMPLE III

Identification of Trait Loci Controlling Plant Height in Soybean

The instant method is well suited to the analysis of many traits of interest in breeding. One such trait in soybean is plant height. Using the same genotypic germplasm survey described in Example I and height data collected in the very same test plots as described in Example I, an analysis of marker loci was conducted to determine which marker loci were associated with and predictive of soybean plant height. As with yield in Example I, each marker locus was tested in separate least squares analyses.

The following analysis of variance model was used to analyze each genetic marker locus:

$$Y_{ijkl} = \mu + \alpha_i + \tau_j + \rho_k + \beta(X_{ij} - X \ldots) + (\alpha\tau)_{ij} + (\alpha\rho)_{ik} + (\alpha\tau\rho)_{ijk} + \epsilon_{ijkl}$$

where:
$Y_{ijkl}$ = height of the $ijkl^{th}$ entry;
$\mu$ = overall mean;
$\alpha_i$ = marker allele effects;
$\tau_j$ = year effects;
$\rho_k$ = maturity effects;
$\beta$ = regression coefficient of Y on X where $X_{ij}$ = test plot height means; and
$\epsilon_{ijkl}$ = error.

The same sixteen RFLP marker loci utilized in Example I were tested for a significant association with plant height using either the northern or southern maturity data sets described in Example II. A marker locus was considered to be linked to and predictive of plant height in either the north or the south if the marker locus F-test was significant at the p<0.05 level. The sixteen marker loci were analyzed independently as described and these sixteen marker loci along with the average heights for each marker allele class are presented in Tables VII and VIII. The model used to analyze each of the sixteen markers was the same with the exception that the numbers of entries, locations, maturity groups, and years would vary depending upon the frequency of missing phenotypic and genotypic data.

In the north, four marker loci were identified as being significantly associated with soybean plant height (Table VII).

TABLE VII

MARKER LOCI ANALYZED FOR SIGNIFICANT ASSOCIATION WITH SOYBEAN PLANT HEIGHT IN NORTHERN MATURITY ZONES (Marker loci which are associated with and predictive of soybean plant height in northern maturity zones are indicated in bold (p < 0.05). Marker loci not indicated in bold (p > 0.05) failed to show an association with soybean plant height. For each allele at marker loci, the predicted average soybean plant height of entries is shown for northern maturities.)

| Locus | Allele | Average Height (in +/- std err) |
|---|---|---|
| 1202 | 1 | 28.869 +/- 0.072 |
|  | 2 | 28.689 +/- 0.091 |
|  | 3 | 29.835 +/- 0.512 |
| 1203 | 1 | 28.588 +/- 0.065 |
|  | 2 | 28.576 +/- 0.059 |
| 1318 | 1 | 28.408 +/- 0.050 |
|  | 2 | 29.036 +/- 0.174 |
| 1329 | 1 | 28.077 +/- 0.154 |
| 1342 | 1 | 28.865 +/- 0.085 |
|  | 2 | 28.663 +/- 0.175 |
| 1443 | 1 | 28.466 +/- 0.054 |
|  | 2 | 28.388 +/- 0.214 |
| 1450 | 1 | 28.607 +/- 0.071 |
|  | 2 | 28.593 +/- 0.947 |
| 1487 | 1 | 28.720 +/- 0.041 |
|  | 2 | 28.594 +/- 0.329 |
| 1492 | 1 | 28.734 +/- 0.052 |
|  | 2 | 28.403 +/- 0.072 |
| 1503 | 1 | 28.531 +/- 0.073 |
|  | 2 | 29.031 +/- 0.360 |
|  | 3 | 29.862 +/- 0.388 |
| 1522 | 1 | 28.683 +/- 0.072 |
|  | 2 | 28.654 +/- 0.055 |
| 1525 | 1 | 28.598 +/- 0.047 |
|  | 2 | 28.725 +/- 0.155 |
| 1529 | 1 | 28.633 +/- 0.042 |
| 1587 | 3 | 28.705 +/- 0.101 |
| 1593 | 1 | 28.803 +/- 0.068 |
|  | 2 | 28.413 +/- 0.664 |
| 1596 | 1 | 28.993 +/- 0.231 |
|  | 2 | 28.624 +/- 0.148 |

These markers were 1202, 1318, 1492, and 1503. Within each marker, least square means average height) for each marker allele were calculated and are shown in Table VII. Those alleles which are predictive of taller plant height have the largest calculated average height. To breed for taller soybean varieties in the north, selection for these genetic marker alleles should be performed.

The same analysis was performed with the southern maturity data set. Only two loci were significantly associated with plant height when the southern data set was analyzed (Table VIII).

TABLE VIII

MARKER LOCI ANALYZED FOR SIGNIFICANT ASSOCIATION WITH SOYBEAN PLANT HEIGHT IN SOUTHERN MATURITY ZONES (Marker loci which are associated with and predictive of soybean plant height in southern maturity zones are indicated in bold ($p < 0.05$). Marker loci not indicated in bold ($p > 0.05$) failed to show an association with soybean plant height. For each allele at marker loci, the predicted average soybean plant height of entries is shown for southern maturities.)

| Locus | Allele | Average Height (in +/- std err) |
|---|---|---|
| 1202 | 1 | 27.891 +/- 0.243 |
|  | 2 | 28.537 +/- 0.374 |
| 1203 | 1 | 28.205 +/- 0.227 |
|  | 2 | 28.029 +/- 0.283 |
| 1318 | 1 | 27.930 +/- 0.328 |
|  | 2 | 29.690 +/- 0.368 |
| 1329 | 1 | 28.377 +/- 0.346 |
| 1342 | 1 | 28.995 +/- 0.600 |
|  | 2 | 29.263 +/- 0.136 |
| 1443 | 1 | 27.846 +/- 0.289 |
|  | 2 | 28.266 +/- 0.399 |
| 1450 | 1 | 27.885 +/- 0.321 |
|  | 2 | 27.386 +/- 0.686 |
| 1487 | 1 | 27.902 +/- 0.282 |
|  | 2 | 28.123 +/- 0.278 |
| 1492 | 1 | 27.899 +/- 0.155 |
|  | 2 | 28.408 +/- 0.345 |
| 1503 | 1 | 27.710 +/- 0.274 |
|  | 2 | 28.331 +/- 0.799 |
|  | 3 | 28.638 +/- 0.279 |
| 1522 | 1 | 28.039 +/- 0.236 |
|  | 2 | 28.157 +/- 0.312 |
| 1525 | 1 | 28.990 +/- 0.235 |
|  | 2 | 28.194 +/- 0.780 |
| 1529 | 1 | 28.071 +/- 0.278 |
| 1587 | 1 | 27.857 +/- 0.365 |
| 1593 | 1 | 28.153 +/- 0.300 |
| 1596 | 1 | 26.885 +/- 0.176 |
|  | 2 | 28.045 +/- 0.318 |

Again, the least square means (average height) for each allele class were calculated. For southern soybean germplasm, selection for allele 3 at marker 1503 and allele 2 at marker 1596 would be expected to result in the tallest soybean varieties.

EXAMPLE IV

Use of Genetic Markers to Select Superior Soybean Plants

Once desired trait locus/marker locus linkage associations have been identified using the instant method, these same genetic marker loci may be used to create new superior varieties. It is first envisioned that that the method will facilitate the selection of parental lines for crossing which have complementary combinations of alleles for superior yield, disease resistance, other plant traits, or a combination of traits. It is also envisioned that the marker loci would be used to disclose the genetic potential of segregants in breeding populations and permit the selection of those lines with the best phenotypic potential.

Selection of parents for the development of superior offspring

It is important to determine lines which when used as parents have the greatest probability of producing offspring with superior performance. These transgressive segregant offspring would result from the crossing of parents with complementary sets of alleles. Using information provided by the method, those genetic marker alleles which predict desired trait performance at a marker locus would be known. By genotyping lines at those marker loci, the value of those lines as parents is revealed. For example, if one wanted to create an individual containing superior alleles at five separate yield loci (A–E), one might want to identify and cross a parent composed of desired alleles for locus A, B, and C with a parent composed of desired alleles at B, D, and E. These parents are complementary because they permit the recovery of progeny containing desired alleles at all five loci. Ideally, parents would be chosen which when combined ensure maximum complementation of loci, so that a high frequency of desired genotypes are recovered.

As an aid to parent selection and as a demonstration of the utility of the instant method, a hypothetical ideal genotype for yield was created using the results from the analysis in Example I (see Table II). This ideal genotype is composed of those genetic marker alleles predictive for high yield as disclosed in the analysis of all maturity groups. A set of elite varieties and their ancestors was then compared against this ideal genotype. The percentage genetic similarity to the ideal genotype was calculated for each line by comparing its genotype to the ideal genotype at significant marker loci. For example if an entry was identical in allelic composition to the ideal genotype for eighteen of twenty alleles (ten loci), then its percentage similarity to the ideal genotype would be 90%. The results are presented in Table IX.

TABLE IX

THE PERCENTAGE SIMILARITY OF ELITE AND ANCESTRAL SOYBEAN VARIETIES TO AN IDEAL GENOTYPE COMPOSED OF SELECTED ALLELES FROM TEN RFLP MARKER LOCI FOUND TO BE SIGNIFICANTLY ASSOCIATED WITH YIELD ACROSS TESTED MATURITY GROUPS

| Variety | Type | % Similarity to Ideal Genotype |
|---|---|---|
| A3127 | Elite | 90.0 |
| A3205 | Elite | 90.0 |
| A4906 | Elite | 87.5 |
| A4271 | Elite | 85.0 |
| A1937 | Elite | 80.0 |
| A3966 | Elite | 75.0 |
| A4997 | Elite | 70.0 |
| A5474 | Elite | 70.0 |
| PI54610 | Ancestor | 70.0 |
| A3307 | Elite | 60.0 |
| CNS | Ancestor | 60.0 |
| Roanoke | Ancestor | 60.0 |
| A4595 | Elite | 55.6 |
| Mukden | Ancestor | 50.0 |
| Tokyo | Ancestor | 40.0 |
| Mandarin | Ancestor | 30.0 |
| A.K. Harrow | Ancestor | 30.0 |
| Manchu | Ancestor | 25.0 |
| Richland | Ancestor | 16.7 |

There is a string correlation between eliteness and similarity to the ideal genotype. The results in Table IX demonstrate that during the development of elite varieties there was an accumulation of those alleles predicted by the method to be desirable for higher yield. By recombining selected elite parents further progress toward the creation of a line genetically identical to the ideal genotype could be mad;. The plant breeder would thus be able to select parents based upon their genetic composition, as revealed by genetic marker loci, with the objective of creating higher yielding lines with a genotype the same as a hypothetical ideal genotype.

Selection of favorable genotypes in a breeding population

In breeding populations, selection for desirable genotypes typically is dependent upon the successful disclosure of superior genotypes through observation of the phenotypes. By analyzing marker loci associated with a trait in segregating populations, marker-based selection can be effectively used to identify and select desired genotypes. Selection of the most desirable genotypes is accomplished by analyzing individuals in populations using these informative marker loci. Favorable genotypes will have the highest frequency of desired alleles and these may be selected once their genotypes are revealed by genetic marker analysis. Also by knowing the number of loci segregating in the cross, the plant breeder can better optimize both the breeding method employed as well as the selection intensity, with the objective of maximizing the recovery of desired genotypes.

What is claimed is:

1. A method for identifying a genetic marker locus that is genetically linked to a trait locus from a crop species and determining the phenotypic value of each allele at the identified genetic marker locus, the method comprising:
   a) providing a map of know genetic markers on a chromosome of a crop species;
   b) genotyping greater than forty entries of a crop species using germplasm of multiple ancestry wherein the entries are not members of a segregating population created solely for the purpose of genetic analysis;
   c) comparing the genotypic data obtained in step b) to phenotypic data collected on the same entries used to create the genotypic data or on progeny of the same entries us d to create the genotypic data;
   d) identifying a genetic marker locus that is linked to a trait locus; and
   e) calculating the mean phenotypic value for each allelic class at the genetic marker locus identified in step d).

2. The method of claim 1 wherein the genotypic data and phenotypic data are collected on entries grown in the same environment.

3. The method of claim 1 or claim 2 wherein the crop species is soybean.

4. The method of claim 1 or claim 2 wherein the trait locus contributes to a trait selected from the group consisting of yield, lodging resistance, height, maturity, disease resistance, pest resistance, resistance to nutrient deficiency and grain composition.

5. The method of claim 1 or claim 2 wherein the genetic marker locus is selected from the group consisting of Restriction Fragment Length Polymorphisms, Simple Sequence Repeats Random Amplified Polymorphic DNAs, AFLPs and allozymes.

6. The method of claim 1 wherein said entries number greater than forty and are representative of more than twenty ancestries.

7. The method of claim 2 wherein the environment is a geographic region.

8. The method of claim 7 wherein the geographic region is defined by a member selected from the group consisting of maturity group, soil type, average rainfall received, average heat units received, growing-degree days and latitude.

* * * * *